United States Patent
Piccirilli et al.

(10) Patent No.: US 7,589,121 B2
(45) Date of Patent: Sep. 15, 2009

(54) USE OF FURAN ALKYLS FOR PREPARING A DRUG FOR TREATING OBESITY AND COSMETICALLY TREATING OVERWEIGHT

(75) Inventors: Antoine Piccirilli, Villennes sur Seine (FR); Philippe Msika, Versailles (FR); Nathalie Piccardi, Arceau (FR)

(73) Assignee: Laboratoires Expanscience, Courbevoie (FR)

( * ) Notice: Subject to any disclaimer, the term of this patent is extended or adjusted under 35 U.S.C. 154(b) by 18 days.

(21) Appl. No.: 11/597,634

(22) PCT Filed: May 27, 2005

(86) PCT No.: PCT/FR2005/001312

§ 371 (c)(1),
(2), (4) Date: Nov. 27, 2006

(87) PCT Pub. No.: WO2005/117857

PCT Pub. Date: Dec. 15, 2005

(65) Prior Publication Data

US 2007/0238777 A1  Oct. 11, 2007

(30) Foreign Application Priority Data

May 28, 2004 (FR) .................................. 04 05782
Mar. 21, 2005 (FR) .................................. 05 02758

(51) Int. Cl.
 *A61K 31/34* (2006.01)
(52) U.S. Cl. ........................................ 514/461; 514/217
(58) Field of Classification Search .................. 514/461
 See application file for complete search history.

(56) References Cited

U.S. PATENT DOCUMENTS

| | | | |
|---|---|---|---|
| 4,127,592 A | 11/1978 | Cohen | |
| 4,594,472 A | 6/1986 | Brettle et al. | |
| 5,262,163 A | 11/1993 | Rancurel | |
| 5,468,490 A * | 11/1995 | Huber et al. | 424/78.03 |
| 6,030,993 A | 2/2000 | Jew et al. | |
| 6,582,688 B1 | 6/2003 | Broutin et al. | |
| 6,994,875 B2 | 2/2006 | Piccirilli et al. | |
| 2003/0120073 A1 | 6/2003 | Seto | |
| 2004/0033506 A1 | 2/2004 | Farrelly et al. | |
| 2005/0048144 A1 | 3/2005 | Han et al. | |
| 2005/0256061 A1 | 11/2005 | Msika et al. | |
| 2006/0122246 A1 | 6/2006 | Msika et al. | |

FOREIGN PATENT DOCUMENTS

| | | |
|---|---|---|
| EP | 0 046 595 A1 | 3/1982 |
| EP | 0 110 548 B1 | 6/1984 |
| EP | 0 775 480 A1 | 5/1997 |
| EP | 1 020 192 A2 | 7/2000 |
| FR | 2 678 614 A1 | 1/1993 |
| FR | 2 678 632 A1 | 1/1993 |
| WO | WO 01/21605 A2 | 3/2001 |
| WO | WO 02/058698 A2 | 8/2002 |
| WO | WO 03/004484 A1 | 1/2003 |
| WO | WO 03/007888 A2 | 1/2003 |
| WO | WO 2004/002435 A2 | 1/2004 |
| WO | WO 2004/016106 A1 | 2/2004 |
| WO | WO 2004/112741 A1 | 12/2004 |

OTHER PUBLICATIONS

Database CA Online Chemical Abstract Service, XP-002312714, Pleshakov et al., "Arylsulfonic acid salts having hypoglycemic activity," Database accession No. 121:73898, Aug. 20, 1994.
Database CA Online Chemical Abstract Service, XP-002312713, Takaya et al., "Lipid metabolism-improving pharmaceutical compositions containing furans or thiophenes for prophylactic and therapeutic treatment of hyperlipidemia," Database accession No. 137:140429, Jul. 31, 2002.
Farines et al., "Influence of Avocado Oil Processing on the Nature of Some Unsaponifiable Constituents," J. of Am. Oil Chem. Soc., 1995, 72(4), 473-476.
Kim et al., "New Antihypercholesterolemic Agents 2. Synthesis and Biological Activity of Ethyl 7-(2-Furyl)-3,5-dihydroxy-1-heptenoate," Korean J. of Med. Chem., 1994, 4(1), 10-15.
Perreault et al., "Targeted disruption of inductible nitric oxide synthase protects against obesity-linked insulin resistance in muscle," Nature Medicine, Oct. 2001, 7(10), 1138-43.
Office Action issued Nov. 18, 2008, in U.S. Appl. No. 11/597,635.
Reusch, "Diabestes, microvascular complications, and cardiovascular complications: what is it about glucose?," J. Clin. Invest., 2003, vol. 112, No. 7, pp. 986-988.
Webster's Dictionary, 1963, Merriam-Webster (Publisher), p. 1798.

* cited by examiner

*Primary Examiner*—Sreeni Padmanabhan
*Assistant Examiner*—Timothy E Betton
(74) *Attorney, Agent, or Firm*—Foley & Lardner LLP

(57) ABSTRACT

The invention relates to the use of one or several synthetic or natural furan alkyls for preparing a drug preventing and/or treating obesity or overweight. The use of one or several synthetic or natural furan alkyls for cosmetically treating local excessive weight is also disclosed. Said furan alkyls preferably correspond to formula (I), wherein identical or different $R_1$, $R_2$, $R_3$ et $R_4$ are independently of each other a hydrogen atom, a $C_1$-$C_{35}$ alkyl radical, $C_1$-$C_{35}$ alcenyl radical or a $C_1$-$C_{35}$ alcynyl radical, preferably $C_{10}$-$C_{22}$, wherein said alkyl, alcenyl and alcynyl radicals are substitutable and $R_1$, $R_2$, $R_3$ are preferably a hydrogen atom.

11 Claims, No Drawings

USE OF FURAN ALKYLS FOR PREPARING A DRUG FOR TREATING OBESITY AND COSMETICALLY TREATING OVERWEIGHT

This application is a National Stage application of PCT/FR2005/001312, filed May 27, 2005, which claims priority from French patent applications FR 0405782, filed May 28, 2004, and FR 0502758, filed Mar. 21, 2005. The entire contents of each of the aforementioned applications are incorporated herein by reference.

The present invention concerns the use of one or more alkylfurans, whether synthetic or natural, to prepare a drug intended to prevent and/or treat diabetes, insulin resistance, obesity, overweight, dyslipidaemia and hence risks of cardiovascular, neural, skin, kidney, eye and infectious diseases. It also concerns the use of one or more natural or synthetic alkylfurans for the cosmetic treatment of localized overweight and/or cellulite and for skin disorders in diabetic persons.

Diabetes is a chronic disease often related to other diseases such as overweight or dyslipidaemia, or to the risk of cardiovascular disease. Diabetes is also a chief cause of blindness in persons aged 25 to 74 years. Those suffering from diabetes are 2 to 4 times more likely to develop heart disease and are 5 times more likely to suffer a stroke. Diabetes is defined as a state of chronic hyperglycaemia: fasting glycaemia of more than 7 mmol/l or 1.26 g/l confirms diabetes. If glycaemia lies between 1.1 and 1.26 g/l, hyperglycaemia must be obtained by oral route. A distinction is made between two main types of diabetes, insulin-dependent diabetes and noninsulin-dependent diabetes. Another form of diabetes also exists that is found in some pregnant women.

Type I, or insulin-dependent diabetes, is also called childhood diabetes since its onset most often occurs at an early age, peaking at 12 years. It concerns 10 to 15% of diabetics. The onset of this form of diabetes is sudden and progresses rapidly. It is considered to be an auto-immune disease, i.e. caused by a disturbance of the immune system which modifies or destroys body cells. The immune system gradually destroys the β cells of the islets of Langerhans in the pancreas which therefore releases increasingly less insulin. When all the β cells are destroyed, insulin is no longer produced. This means that glucose, although available in sufficient quantity, cannot be transported in the cells to produce energy. To offset this deficiency, it is vital to inject insulin to prevent an increase in glycaemia. Insulin cannot be taken by oral route since it is inactivated by the stomach. The exact cause of this type of diabetes is unknown.

Type II or noninsulin-dependent diabetes, is the most frequent form (nearly 90% of cases), this form being less serious than the previous form and having a progressive onset. Onset is generally in adulthood, after the age of 40, and is often related to overweight. In most Type II diabetics the pancreas produces sufficient and even excess insulin. In this case, the pancreas does produce insulin but not in time or insufficiently for needs, or else the body reacts by resisting against insulin. Although the body produces a sufficient amount of insulin, the cells cannot react normally since the recognition sites located on the surface of the cell are modified. Insulin is no longer recognized and glucose is no longer able to enter in sufficient quantity into the cells to produce energy. Too much glucose remains in the blood giving rise to a high glycaemia level. The pancreas, responsible for regulating the metabolism of glucose, responds to this disturbance by producing more insulin. This is the start of a vicious circle: the pancreas produces increasingly more insulin so that the cells can nevertheless be provided with glucose. This is why Type II diabetes firstly exhibits a high insulin level. The recognition sites must be modified so that insulin can be recognized. Most Type II diabetics can achieve this through losing weight and increasing physical activity. In more advanced cases, treatment in tablet form is necessary. These persons carry an increased risk of developing heart disease and hypertension.

Another type of diabetes also exists called Gestational Diabetes Mellitus (GDM), only found in pregnant women whose hyperglycaemia or impaired glucose tolerance occurs or is diagnosed for the first time during pregnancy and subsides at the end of the postpartum period. Women with known diabetes who become pregnant do not enter into this category. Gestational diabetes is frequent and is found in 6% of pregnancies. It exposes the mother and foetus to numerous risks, such as an increase in pregnancy hypertension, pre-eclampsia, caesarean section, that are more severe the earlier their onset and if hyperglycaemia is ill managed. In children, it increases the risk of neonatal death, macrosomia, obstetrical injury, respiratory distress, neonatal hypoglycaemia, hyperbilirubinaemia and hypocalcaemia. In addition to short term complications, women who have suffered gestational diabetes show an increased risk, 10 to 15 years later, of developing Type II diabetes. Their children carry a risk of obesity and probably of diabetes over the longer term. Studies have shown that serum and amniotic liquid levels of magnesium in diabetic mothers are abnormally low. This hypomagnesaemia affects the foetus and may cause congenital malformations and early neonatal hypocalcaemia. Treatment entails a diet, then if the glycaemia is not regulated and exceeds 7.8 mmol/l after a meal, the administering of insulin becomes necessary.

In addition, diabetes has major consequences on the skin, in particular Type II diabetes. It is known that sugars bind to proteins by Maillard reaction leading to advanced glycation end products (AGE) which globally increase ageing of the skin and tissues. Recently, it was shown that lipids play an initiator role in this irreversible reaction, and that genetic factors contribute towards individual susceptibility. The highest AGE levels are found in slow renewal tissues such as the tendons, bone, skin, cartilage and amyloidal tissues. These AGE products affect the mechanical properties of the matrix (reduced elasticity) and limit tissue renewal. Also, an increase in matrix metalloproteases (MMP-2/3) has been evidenced as well as serious microcirculation disorders which are essential elements in the genesis of diabetic foot ulcers, a pathology caused by lack of healing against a picture of chronic inflammation. Recently, evidence was shown of reduced water levels in the skin barrier of diabetics, of reduced epidermal cell proliferation and modulated desquamation, pointing to a major disorder in skin barrier protection similar to aged, irritated or xerotic skin. Diabetes also limits the capacity to react against bacterial and fungal infection, which may transform minor injuries into serious infections going as far as amputation of the foot if left uncared.

One of the main causes of noninsulin-dependent diabetes (Type II diabetes) is obesity, without this disorder being invariably linked to diabetes. The adipose cells increase insulin requirements and obese persons develop a resistance to the action of insulin. The blood glycaemia or sugar level then constantly remains high, causing diabetes. Obesity may also aggravate insulin-dependent (Type I) diabetes. It is estimated that an obese person carries twice the risk of suffering from diabetes than persons of normal weight. Recent work, conducted by a team at Laval University, has evidenced that mice whose iNOS gene (inducible enzyme producing nitric oxide) is genetically deleted are protected against the development of diabetes associated with obesity (Nat Med 2001, October; 7(10):1138-43. Targeted disruption of inducible nitric oxide synthase protects against obesity-linked insulin resistance in muscle. Perrault M, Marette A).

In addition to its link with Type II diabetes and gestational diabetes, obesity is currently the second factor after ageing in the aetiology of chronic pathologies. In 2004, approximately 64% of the adult American population suffered from overweight. It is estimated that in 2008, 34% of adult Americans will be obese. Obesity is an excessive body fat index arising from an imbalance between daily calorie intake and energy expenditure: the body receives more than it uses and therefore "stores" part of the surplus. However, numerous factors may accentuate this imbalance paving the way for obesity or at least a weight gain: heredity, food habits, sedentary lifestyle, discontinued smoking, hormonal phenomena (in particular in women and the younger population), medication and the socio-professional background . . . . In less than 3 years, 650 000 new cases of obesity have been recorded in France. In Europe, and depending on countries, the increase in the number of obese persons varies between 10 and 40%. This record level of 40% is reached in women in Eastern European countries, in Tunisia where 40% of persons over the age of 30 suffer from obesity. A phenomenon for concern is child obesity, which is sharply rising. A study in France in children aged 10 months to 8 years has shown that 10% were obese instead of the expected 3%. In Japan, child obesity has jumped by 53%, in England by 65% for some age groups, and in the USA by 60%.

This worrying trend is the source of numerous complications with endocrinal, cardiovascular and psycho-social consequences (discrimination, reduced quality of life, pain) which require management and hence a diagnosis that is as early as possible. For example, overweight increases the risk of death from cardiovascular disease (50 to 80%), of diseases associated with high morbidity and death rate (Type II diabetes which could be decreased by 30 to 45%), of arterial hypertension, of metabolic, joint and vesicular disorders, and of some cancers (colon, rectum, prostate, uterus, breast and vesicle). Today there is therefore a major need for medication adapted to treat diabetes and/or obesity.

Within the scope of the present invention, weight loss preferably aims at combating localized overweight. This localized overweight is substantiated in the form of fat whose quantity and distribution differs according to sex. Adipose tissue represents 20 to 30% of body weight in women and 10 to 15% in men. Subcutaneous fat is twice as thick in women as in men. In men, fat accumulates around and above the waist (android distribution, factor of metabolic risk), and in women below the waist in the gluteo-femoral region (gynoid distribution, non-correlated with vascular risk). One of the characteristics of this accumulated fat in the lower half of the body is that it is difficult to move. It is intended to ensure the energy needs of reproduction (pregnancy and especially breast-feeding) and therefore forms the largest reservoir for the body's energy needs.

At cell level, the adipocytes are spherical cells whose intracellular space is taken up by a large vacuole filled with triglycerides. Adipocytes may change volume rapidly. Depending upon circumstances these cells may reach 40 μm to 120 μm in diameter, corresponding to a 27-fold volume increase. In some extreme cases, this increase may be 40-fold. Therefore the adipocyte is the main energy player in the body since it is able to rapidly store (capture or lipogenesis) or conversely to mobilise (lipolysis) the triglycerides, the body's major energy sources. Lipogenesis entails the synthesis of triacylglycerols resulting from esterification of glycerol-3-phosphate by activated fatty acids; conversely, lipolysis corresponds to hydrolysis of stored triacylglycerols into glycerol and fatty acids. Different mechanisms have been evidenced which control lipolysis and lipogenesis, involving receptors such as the alpha-2 and/or beta-1 and -2 receptors for example, type A1 adenosine receptors, prostaglandin E2, Y2 of type YY, and the NPY neuropeptide, but also sexual hormones.

Therefore, knowledge of the mechanisms controlling adipocyte lipolysis and lipogenesis has vastly improved. However, active ingredients for slimming are still being researched since known active ingredients are not fully satisfactory. There is therefore a true current demand for preparing topical compositions which can efficiently help towards slimming.

Cellulite, or localized lipodystrophy, is characterized by an oedematous infiltration of the adipose tissue which alters the appearance and harmony of body shape. If for, various reasons such as over-rich food, inactivity and/or ageing, a considerable imbalance is set up in the body between lipogenesis and lipolysis, i.e. more precisely if the quantities of fat formed by lipogenesis become remarkably and a constantly higher than the quantity eliminated by lipolysis, an accumulation of triglycerides occurs in the adipocytes, and if this accumulation becomes excessive it may translate as localized overweight and/or progressively as thickening of the surface skin often irregular and with a so-called "orange-peel effect" whose consistency is flabby or gelatinous, generally causing an unsightly body shape. This cellulite tissue also affects men but is distinctly more frequent in women whether slim or well built. Fat is preferably localized on the lower half of the body, on the hips, thighs, stomach, and also the knees and ankles. Cellulite results in particular from the storing of triglycerides in the adipocytes, and from an increase in the viscosity of the fundamental substance of the dermis, which translates as water retention and reduced cell exchange. These two mechanisms lead to compression of the blood and lymphatic vessels, and to tissue congestion.

Surprisingly, the inventors have discovered that alkylfurans, whether synthetic or natural, can be used to treat diabetes and obesity. The inventors have also discovered that the application of a topical composition containing these alkylfurans has a slimming action, and in particular can be used to combat localized overweight and/or cellulite.

The subject of the present invention is therefore the use of one or more alkylfurans, whether synthetic or natural, to prepare a drug intended to prevent and/or treat diabetes, in particular Type II diabetes.

Under the present invention, through use of the term "drug" is meant both substances or compositions having curative or preventive properties for diseases in Man, and veterinary compositions of prophylactic or curative intention.

The alkylfurans of the invention are able to reduce blood glucose (glycaemia) and to increase glucose tolerance. They can therefore be used to prepare a drug or food supplement, or can be used in everyday food to prevent and/or treat diabetes being intended to regulate lipaemia and/or glycaemia and/or insulin sensitivity.

A further subject of the present invention is the use of one or more synthetic or natural alkylfurans to prepare a drug intended to regulate lipaemia and/or glycaemia and/or insulin sensitivity. The drug is also intended to reduce body fat mass.

Lipaemia corresponds to the blood level of total lipids circulating in the form of lipoproteins and free fatty acids. The presence in the blood of this variety of lipids, also called triglycerides, may be a sign of diabetes. The alkylfurans of the invention are able to reduce the level of circulating triglycerides.

Glycaemia corresponds to the concentration of glucose measured in the blood. Below a certain threshold hypoglycaemia occurs. Above a certain threshold it becomes hyperglycaemia. Reference glycaemia is usually the fasting level measured in the morning. However it may be helpful to measure other pre-prandial glycaemia levels i.e. before lunch or supper, or postprandial glycaemia levels i.e. those measured after a meal (normally 1 h 30 later) which give indications on the highest glycaemia levels during the day.

The inventive alkylfurans are able to reduce the levels of triglycerides in the liver and muscles, thereby enabling limitation of stored fats. The inventive alkylfurans also increase the blood level of high density lipoprotein (HDL) i.e. good cholesterol.

The inventive alkylfurans also enable an increase in energy expenditure (increase of PGC-1 in the muscles—cf. example 9).

A further subject of the present invention is the use of one or more, synthetic or natural, alkylfurans to prepare a drug intended to prevent and/or treat obesity.

According to one advantageous variant of the invention, said alkylfurans meet the following general formula:

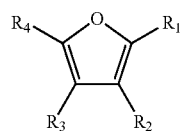

(I)

wherein $R_1$, $R_2$, $R_3$ and $R_4$, the same or different, separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$; a $C_1$-$C_{35}$ alkenyl radical, advantageously $C_{10}$-$C_{22}$, more advantageously $C_{12}$-$C_{20}$, further advantageously $C_{13}$-$C_{17}$; or a $C_{1-35}$ alkynyl radical, advantageously $C_{10}$-$C_{22}$, more advantageously $C_{12}$-$C_{20}$, further advantageously $C_{13}$-$C_{17}$, said alkyl, alkenyl and alkynyl radicals possibly being substituted by one or more halogens and/or by one or more functions chosen from the group consisting of epoxy, hydroxyl (—OH), thiol (—SH), ether (—OR$_5$), primary amine (—NH$_2$), secondary amine (—NHR$_5$), tertiary amine (—NR$_5$R$_6$), aldehyde (—CHO), ketone (—COR$_5$), acetyl (—O—CO—R$_5$) functions wherein $R_5$ and $R_6$ separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$, or a $C_1$-$C_{35}$ alkenyl radical, advantageously $C_{10}$-$C_{22}$, more advantageously $C_{12}$-$C_{20}$, further advantageously $C_{13}$-$C_{17}$.

Under the present invention, the preferred alkyl furans are those which are monosubstituted at position 2. Therefore, said alkylfurans are advantageously synthetic or natural 2-alkylfurans meeting the general formula (1) in which $R_1$, $R_2$, $R_3$ represent a hydrogen atom and $R_4$ does not represent a radical such as previously defined other than the hydrogen atom.

According to one advantageous variant of the invention, said alkylfurans are natural 2-alkylfurans, present in particular in the furanic unsaponifiable matter of avocado, meeting general formula (1) wherein $R_1$, $R_2$, $R_3$ represent a hydrogen atom and $R_4$ represents a radical chosen from the group consisting of the following radicals (*—$R_4$):

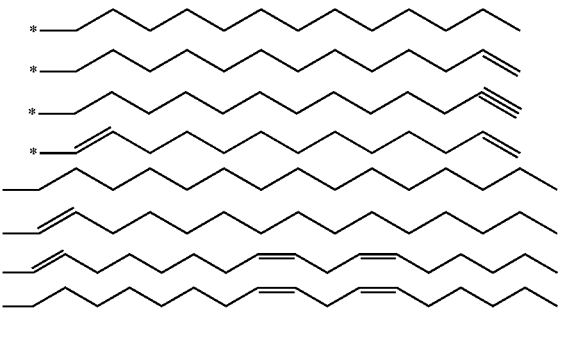

In the furanic unsaponifiable matter of avocado, 2-alkylfurans represent 30% to 70% by weight of this unsaponifiable matter with respect to the total weight thereof. Avocado oil can contain 2 to 4% by weight of 2-alkylfurans with respect to the total weight of the oil.

According to one advantageous variant of the invention, a purified furanic fraction of avocado unsaponifiable matter is used containing 70 to 100 weight %, advantageously 90 to 100 weight % of 2-alkylfurans with respect to the total weight of the fraction, to prepare a drug intended to prevent and/or treat diabetes, in particular Type II diabetes.

According to another advantageous variant of the invention, a purified furanic fraction of avocado unsaponifiable matter is used containing 70 to 100 weight %, advantageously 90 to 100 weight %, of 2-alkyl furans with respect to the total weight of the fraction, to prepare a drug intended to prevent and/or treat obesity.

According to another advantageous variant of the invention, a purified furanic fraction of unsaponifiable avocado is used containing 70 to 100 weight %, advantageously 90 to 100 weight % of 2-alkyl furans with respect to the total weight of the fraction, to prepare a drug intended to regulate lipaemia and/or glycaemia and/or insulin sensitivity.

The unsaponifiable matter is the fraction of a fat which, after extended action by an alkaline base, remains insoluble in water and can be extracted with an organic solvent. Five major groups of substances are present in most unsaponifiables of vegetable oils: saturated or unsaturated hydrocarbons, aliphatic or terpene alcohols, sterols, tocopherols, carotenoid and xanthophyll pigments. The furanic derivatives of avocado oil are compounds known to persons skilled in the art and are described for example by Farines. M et al, 1995, J. of Am. Oil Chem. Soc. 74; 473. The unsaponifiable matter of avocado, rich in furanic lipids has already been described for its use in the manufacture of a drug having a beneficial and curative action on connective tissue, in particular for the treatment of inflammatory pathologies such as arthritis, periodontitis and scleroderma. Under the present invention, for the furanic unsaponifiable matter of avocado, the expressions "alkylfuran(s)" and "furanic lipid(s)" are synonymous expressions.

The avocado is generally chosen from among the following varieties: Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Red, more advantageously the varieties Hass, Fuerte and Reed. Preferably the Hass, Fuerte, Ettinger and Bacon varieties are chosen, and further advantageously the Hass and Fuerte varieties.

In the purified furanic fraction of avocado unsaponifiable, such as developed by Laboratoires Expanscience (cf. international application WO 01/21605), 2-alkylfurans represent 70 to 100 weight % of the total weight of the fraction, and the relative weight proportions of each of the identified furans are given in Table I below:

TABLE I

| 2-alkylfurans composition of the purified furanic fraction of avocado unsaponifiable matter | Wt. % |
|---|---|
| 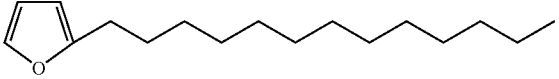 | 3-12 |
| 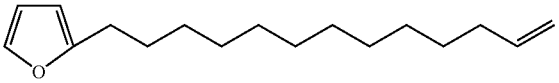 | 1-8 |
| 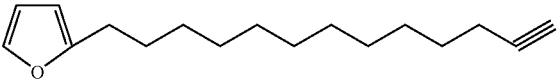 | 1-5 |
| 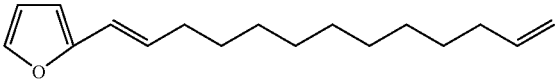 | 1-6 |
| 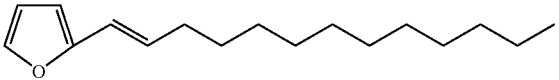 | 5-20 |
| 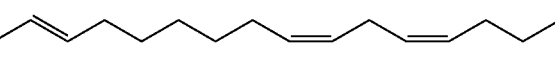 | 10-30 |
| 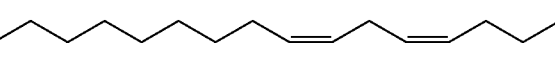 | 35-75 |

In international application WO 01/21605, Laboratoires Expanscience applied a specific process making it possible to obtain a selective extraction of avocado furanic lipids having a furanic lipid content of more than 80% by weight, even close to 100%. This process comprises the steps consisting of preparing unsaponifiable avocado matter and subjecting this unsaponifiable matter to a molecular distillation step using temperature and pressure means adjusted to obtain a distillate chiefly containing furanic lipids of avocado.

Preferably, the unsaponifiable avocado matter is prepared from the previously heat-treated fruit, before oil extraction and saponification, as described in particular in patent application FR-91 08301. This heat treatment consists of controlled drying of the fruit, preferably the fresh fruit, for at least four hours and advantageously for between 24 and 48 hours, at a preferred temperature of at least around 80° C. and preferably ranging from around 80 to 120° C.; temperature and drying time being dependent on each other. Before its saponification, the oil can be previously enriched with unsaponifiable matter by separating a majority of the constituents of the unsaponifiable matter which are collected in a concentrate. Different methods may be used: cold crystallization, liquid-liquid extraction, molecular distillation. Molecular distillation is particularly preferred, and is advantageously conducted at a temperature of between approximately 180 and approximately 230° C., maintaining a pressure of between $10^{-3}$ and $10^{-2}$ mmHg. The unsaponifiable avocado matter, obtained as described above, is then subjected to a molecular distillation step. This molecular distillation step is conducted with temperature means adjusted to a temperature of between 100 and 160° C. and pressure means adjusted to a pressure of between $10^{-3}$ and $5.10^{-2}$ mmHg. In particular, the temperature means are adjusted for a temperature of between 100 and 140° C. and the pressure means are adjusted for a pressure of between $10^{-3}$ and $5.10^{-2}$ mmHg to obtain a distillate chiefly containing furanic lipids of avocado.

In international application WO04/016106, Laboratoires Expanscience developed a process with which it is possible to obtain a high yield of unsaponificable avocado matter rich in furanic lipids, i.e. varying from 50 to 80% and with a low content of heavy products and peroxides. This process comprises the following successive steps:
(1) a controlled dehydration step of fresh or previously processed avocados, conducted at a temperature of between −50° C. and 75° C.,
(2) an extraction step to extract the oil from the dehydrated fruit,
(3) alternative steps of:
  a. heat treatment of the extracted oil at a temperature possibly varying between 80 and 150° C., optionally in an inert atmosphere, followed by a concentration step of the oil into its unsaponifiable fraction, or else:
  b. concentration of the oil into its unsaponifiable fraction followed by heat treatment at a temperature possibly varying between 80 and 150° C., optionally in an inert atmosphere, followed by:
(4) a saponification and extraction step of the unsaponifiable matter.

By dehydration at step (1) of the process is more generally meant all techniques known to those skilled in the art which can be used to extract water from a compound. Amongst these techniques preference is given to drying in ventilated driers in thin layers and under a stream of hot air, at a temperature of between 70 and 75° C. for 8 to 36 hours. The heat treatment step implemented at step (3)a. or (3)b. can be conducted with or without an acid catalyst, preferably acid aluminas. The concentration step at step (3)a. or (3)b. can use cold crystallization or molecular distillation.

Alternatively, the preparation of an unsaponifiable fraction of avocado consisting of alkyl furans may use raw materials which are co-products derived from avocado oil extraction methods. In particular oils extracted from fresh fruit, with no prior drying of the fruit. Amongst these co-products a non-exhaustive list comprises: i) fatty phases and ii) aqueous phases derived from so-called centrifuging processes, or those derived from so-called "enzymatic" processes which in particular comprise an enzymatic pre-digestion step of the pulp plant cells to facilitate release of the lipids from the fruit. The solid residues of centrifuging (centrifuge deposits) after drawing off crude oils may also form a raw material of interest. Also, again alternatively, the frozen pulp of previously peeled and seeded fruit may be used. Similarly, deodorization releases from avocado oils also form sources of avocado unsaponifiable matter and alkylfurans. Avocado cake co-produced during mechanical cold pressing of the fruit (fresh or dried) or during liquid-liquid extraction of avocado oil using a solvent may, as such, form an alternative raw material. Finally, although having low oil content, avocado seeds may potentially form a source of avocado lipids, and of alkylfurans in particular.

Under the present invention, the purified alkyl furans are advantageously used in a proportion of between 0.001 and 100% by weight, preferably between 0.5 and 60% of the total weight and further preferably between 2% to 25% by weight with respect to the total weight of the drug. The quantity of inventive drug to be administered depends on the severity of the disorder being treated and on the time since its onset. Obviously the doctor will also adapt dosage in relation to patients. According to one advantageous variant of the invention, the daily therapeutic dose of inventive alkylfurans advantageously ranges from 10 mg to 30 g/day preferably from 60 mg/g to 10 g/day and more particularly from 100 mg/day to 6 g/day, or approximately 0.160 to 500 mg/kg/day preferably 1 mg/kg/day to 160 mg/kg/day and more particularly 16 mg/kg/day to 100 mg/kg/day.

In association with the drug of the invention, advantageously with synergic effect, hypolipaemic treatments may be used, such as sterol chelators (colestyramine), fibrates (fenofibrate: PPAR-alpha agonist), inhibitors of hmg-coA reductase (lovastatin, simvastatin), EPA/DHA (fish oil containing omega 3, EPA=eicosapentaenoic acid, DHA=docosahexaenoic acid), gene therapy, treatments for hypercholesterolaemia of various origins (primary, monogenic, polygenic, alpha-lipoproteinaemia), treatments for mixed hyper-lipidaemia, treatments for hypertriglyceridaemia, treatments for dyslipidaemia. The treatments generally used may be nutrition (Mediterranean diet and controlled intake), pharmacology by ion exchange resins, fibrates, statins, fish oils, antioxidants, phytosterols or stanols.

In association with the drug of the invention, advantageously with synergic effect, anti-diabetic treatments may be used such as oral diabetic treatments, insulin therapy for Type II diabetes and/or various treatments such as glucose captors and an artificial pancreas. As an example of oral diabetic treatment, mention may be made of stimulated insulin secretion (hypoglycaemic sulfamide) or similar (tolbutamide, carbutamide, glicazide, glimepiride, glipizide, derivative of metformin, benfluorex), the inhibition of alpha-glucosidase (acarbose and miglitol), the treatment of insulin resistance (thiazolidinediones or glitazone) such as rosiglitazone and pioglitazone, or treatments for obesity such as inhibitors of serotonin uptake (sibutramine), inhibitors of lipid digestion (orlistat) agonists of the adrenergic Beta3 receptor (increases lipolysis and thermogenesis) or the increased peripheral use of glucose (by reduced oxidation of fatty acids), or insulin secretion with GPI, pramlintide, IGFI and the derivatives of vanadium, glinides.

In association with the drug of the invention, advantageously with synergic effect, use may be made of drugs intended for the treatment of cardiovascular disease (arterial, coronary and cerebral hypertension and secondary arteriopathy) and/or bronchopulmonary and rheumatological complications, cancer, liver impairment.

The drug of the invention may also, in association and advantageously with synergic effect, comprise hypoglycaemic plants or foods, trace elements in particular chromium pidolate, antioxidants, PPAR agonists whether natural or not, sterol unsaponifiables or products possibly containing the same (vegetable oil unsaponifiables, in particular soy oil unsaponifiables, plant butter or butyric unsaponifiables and their mixtures, unsaponifiables of natural wax, unsaponifiables of oil extracts, unsaponifiables of industrial oil co-products, unsaponifiables of animal fat extracts, unsaponificables of marine oils, unsaponifiables of lactic fat extracts, unsaponifiables of lipids extracted from unicellular organisms, unsaponifiables of lipids extracted from algae and marine organisms, etc), sterols, stanols, phytosterols, phytostanols, tocopherols, concentrates of sunflower, rapeseed and/or palm oil, omega 3, 6 or 9 fatty acids, anti-fat nutrients. "Sterol" unsaponifiables are unsaponifiables whose content of sterols, methylsterols and triterpene alcohols ranges from 20 to 95% by weight, preferably 45-65% by weight with respect to the total weight of the unsaponifiable. Hypoglycaemic plants which may be used under the present invention in association with the alkylfurans are advantageously chosen from the group consisting of fenugreek (*Trigonella graenum*), corosolic acid (active compound of leaves of the *Lagestroemia speciosa* tree), *Gymnema sylvestra*, the juice of the momordica fruit (*Momormodica charantia*), eucalyptis (*Eucalyptus globulus*), *Panax ginseng*, blueberry leaves (*Vaccinium myrtillus*).

The alkylfurans can be used in association, advantageously with synergic effect, with hyperglycaemic foods or treatments to restore glycaemic balance, such as antiretroviruses, glucocorticoids, immunosuppressants, IFN-Alpha, sexual steroids, THS, the pill, growth hormones, sympathomimetics, cardiovascular medicines, diuretics, Beta-blockers, calcium inhibitors, psychotropics.

The alkylfurans can be used in association, advantageously with synergic effect, with hyperlipaemic drugs or foods, causing weight gain, to reduce the overall risk thereof and/or in association with hypolipaemic drugs or foods to reduce weight, to act on glycaemia and achieve a broader spectrum of efficacy.

Mucilage plants may play an important role in the treatment of hyperglycaemia since they have a favourable effect on overweight and excessive pancreas secretion. The hydrophilic properties of mucilage fibres, by forming a gel, reduce the uptake of carbohydrates and lipids.

The trace elements which can be used under the present invention, in association with the alkylfurans, are advantageously chosen from the group consisting of magnesium, chromium, selenium and their mixtures. The antioxidants which can be used under the present invention, in association with the alkylfurans, are advantageously chosen from the group consisting of zinc, lipoic acid, either alone or combined with vitamin B12, vitamin C, flavonoids (green tea . . . ), beta carotene, lycopene or lutein, antiglycation substances such as carnosine, N-acetyl-cysteine, soy isoflavones, soy proteins.

An increase in oxidative stress in diabetics has been shown via a variety of mechanisms induced by the increase in blood sugar levels. In addition, it is thought that this increase in oxidative stress contributes to the development of diabetic complications such as lesions on large and small vessels (macro and micro-angiopathy).

Drugs containing sulfonylurea and glinides help the pancreas to produce more insulin. Sulfonylureas increase insulin levels for several hours. Glinides, taken with meals, increase insulin levels for a shorter period than sulfonylureas. Low glycaemia is one of the possible effects of these treatments. Drugs containing alpha-glucosidase inhibitors slow down digestion and the absorption of starch and sugars, leading to slowing of glycaemia after meals. Amongst the usual side effects of these treatments, gases and flatulence may be mentioned; however the doses can be increased very gradually to reduce these side effects. Drugs containing biguamides (metformin) act chiefly on the liver. They essentially prevent the liver from producing new sugars when it is not necessary. Biguamide drugs can cause side effects, the most frequent being stomach pain and nausea. To reduce these side effects, it is advisable to take biguamides with meals.

Drugs containing activators of insulin sensitivity or thiazolidinediones (TZD, pioglitazone, rosiglitazone) which are PPAR agonists, are new types of treatment. This new type of oral treatment is described as an insulin sensitivity activator or a TZD. These drugs treat resistance to insulin, one of the main causes of diabetes. Insulin resistance is a condition in which the body does not properly use the insulin it produces. By reducing resistance to insulin, a TZD allows the insulin, whether produced or administered, to function more efficiently and thereby contributes to reducing a dangerous increase in glycaemia. Amongst the possible side effects of TZDs mention may be made of weight gain, the formation of oedema (water retention) and slight anaemia.

The hypolipaemics which may be used under the present invention, in association with the alkylfurans, are advantageously chosen from the group consisting of hypolipaemics of the statin family or fibrate family (PPARα agonists). The anti-obesity drugs which may be used under the present invention, in association with the alkylfurans, are advantageously chosen from the group consisting of orlistat (Xenical®) and sibutramin (Reductyl®) or Sibutral®). Former appetite-suppressant drugs (amphetamines, fenfluramine) are no longer used as they had too many side effects. In France, only two drugs have been given marketing authorization for the treatment of obesity: orlistat (Xenical®) and sibutramin (Reductyl® or Sibutral®). Orlistat (Xenical®) has the effect of hindering the enzyme responsible for fat absorption in the digestive tube. It therefore prevents the absorption of approximately 30% of food fats (triglycerides), which is the equivalent of a calorie reduction of 150 to 200 calories/day for a daily intake of 1800 calories. Non-absorbed fat is eliminated in the faeces. Sibutramin (Reductyl® or Sibutral®) is a molecule acting on the brain neurotransmitters which play a role in controlling food intake. It has the property of reinforcing the feeling of fullness and reduces food intake.

Anti-fat nutrients which may be used under the present invention together with the alkylfurans, advantageously with synergic effect, are advantageously chosen from the group consisting of nutrients blocking the absorption of fats, such as chitosan which is a fibre extracted from the exoskeleton of crustaceans, nutrients able to increase thermogenesis ("fat burners") such as ephedrine (Ma Huang Chinese herb), caffeine, theme and citrus aurantium, CLA (conjugate linoleic acid, preferably derived from safflower oil), fish oils rich in omega 3, lipid capturing cactus palm, dry extracts of nutrients able to regulate appetite ("appetite suppressants") such as L-phenylalanine and L-tyrosine, nutrients able to regulate glycaemia such as minerals e.g. chromium, vanadium or magnesium or the ayurvedic herb *Gymnema sylvestra*, lipogenesis inhibitors such as hydroxycitric acid extracted from *Garcinia cambogia* and nutrients able to transport fats such as L-carnitine.

A further subject of the present invention is the use of a cosmetic composition and/or nutraceutical composition containing one or more alkylfurans, whether natural or synthetic, for the cosmetic treatment of disorders related to overweight.

A further subject of the present invention is the use of a cosmetic composition and/or nutraceutical composition, containing one or more natural or synthetic alkylfurans, for the cosmetic treatment of cellulite.

Overweight, under the present invention, is characterized by excess weight with respect to the non-pathological "ideal weight". The cosmetic treatment of the invention makes it possible to lose or slim down excess localized fat, but is not identified as a therapeutic treatment.

The topical application of a cosmetic composition, containing one or more natural or synthetic alkyl furans, may prove to be particularly advantageous in pregnant women or women who gave birth less than 6 months previously. A further subject of the present invention is a cosmetic treatment method to promote slimming, and in particular to combat localized overweight in pregnant women or women who gave birth less than six months previously. One of the advantages of the compositions which can be used within the scope of the invention is that alcohol is not required for the formulation, which is contra-indicated in pregnant and nursing women on account of its toxicity. Caffeine, a currently much used slimming agent, requires solubilisation in alcohol which is avoided by the present invention.

By "slimming" or "combating localized overweight" under the present invention is meant an action making it possible to prevent or at least reduce the formation of subcutaneous fat such as described above. This action translates in particular as a reduction in unsightly excess or reserve fat, as slimming of body shape, as the accelerated elimination of excesses, as a better-defined body contour or a re-sculpted figure. By "cosmetic treatment to combat localized overweight" under the present invention is meant the use of a cosmetic treatment with which to measure visibly the above-described action. For example, a topical cosmetic composition containing one or more synthetic or natural alkylfurans used according to the invention, can be applied to skin areas likely to form these localized accumulations of fat, namely areas where these accumulations have already formed or are in the progress of being formed.

Under the invention, said alkylfurans used as active ingredients in the cosmetic and/or nutraceutical composition are such as defined previously.

Under the present invention, the alkylfurans are advantageously used in a proportion of between 0.001 and 25% weight % with respect to the total weight of the cosmetic composition, further advantageously between 1 and 10 weight %.

The food supplement may contain 0.001 to 100 weight % of the inventive alkylfurans. In a food, the concentrations of pure alkylfurans which may be used may range from 0.001 to 10 weight % with respect to the total weight of the food.

The cosmetic and/or nutraceutical composition of the invention may also, in association and advantageously with synergic effect, contain hypoglycaemic plants, trace elements, antioxidants, anti-fat nutrients, sterol unsaponifiables or products containing the same, sterols, stanols, phytosterols, phytostanols, tocopherols, concentrates of sunflower, rapeseed and/or palm oils, omega 3, 6 or 9 fatty acids such as described previously.

The drug of the invention and the cosmetic composition may be formulated in the form of different preparations adapted for oral or topical administering. The nutraceutical composition of the invention may be formulated in the form of different preparations adapted for oral administering, or in food form.

When the drug, the cosmetic or nutracaeutical composition are administered per os, they may be administered in unit or multidose forms mixed with suitable pharmaceutical, cosmetic or food vehicles known to persons skilled in the art. The suitable unit forms particularly include tablets optionally scored tablets, capsules, powders, granules and oral solutions or suspensions. The suitable multidose forms particularly include drinkable drops, emulsions and syrups. When preparing the tablets, the inventive alkylfurans are mixed with an acceptable vehicle such as gelatine, talc, starch, lactose, magnesium stearate, gum Arabica or their analogues. The tablets may optionally be coated i.e. coated with several layers of various substances such as sucrose so that they are more pleasant to take, or to facilitate storage. The tablets may also have a formulation of greater or lesser complexity intended to modify the rate of release of the active ingredient. The release of the active ingredient of said tablet can be accelerated, slowed or delayed in relation to the desired absorption. A capsule preparation is obtained by mixing the alkylfurans of the invention with a dilutant. The mixture obtained is poured into soft or hard capsules. A preparation in syrup form may contain the alkylfurans of the invention together with a sweetener, advantageously calorie-free, a flavouring agent and a suitable colouring agent. The water-dispersible powders or granules may contain the alkylfurans of the invention in a mixture with dispersion agents or wetting agents, suspending agents, such as polyvinylpyrrolidone, or sweeteners or taste correctors.

According to one variant of the present invention, the drug and the cosmetic composition may be intended for external topical use. They may also contain a pharmaceutically or cosmetically acceptable vehicle. The drug or cosmetic composition of the invention may be in any of the galenic forms usually used for external topical application Advantageously, according to the present invention, the drug or cosmetic composition are in the form of an aqueous, hydro-alcohol or oil solution, an oil-in-water emulsion or water-in-oil emulsion or multiple, an aqueous or oil gel, a liquid, paste or solid anhydrous product, or an oil dispersion in an aqueous phase using spheres, the spheres possibly being polymer nanoparticles such as nanospheres, and nanocapsules or even better lipid vesicles of ionic and/or non-ionic type. The drug or cosmetic composition may be more or less fluid, be in the form of a white or coloured cream, ointment, milk, lotion, salve, serum, paste, foam, aerosol or stick.

The drug or cosmetic composition of the present invention may also contain the usual additives used in the pharmaceutical and/or cosmetic area such as hydrophilic or lipophilic gelling agents, hydrophilic or lipophilic active ingredients, preserving agents, antioxidants, solvents, perfumes, fillers, chemical or mineral filters, pigments, chelating agents, odour absorbers, spa water and colouring agents. The quantities of these different additives are those conventionally used in pharmaceutics and/or cosmetics, e.g. 0.01 to 20% by weight, with respect to the total weight of the drug or cosmetic composition. These additives, according to their type, may be added to the fatty phase, aqueous phase, lipid vesicles and/or to the nanoparticles.

When the drug or cosmetic composition of the present invention is an emulsion, the proportion of the fatty phase may range from 5 to 80% by weight, preferably from 5% to 50% by weight with respect to the total weight of the composition. The oils, emulsifiers and co-emulsifiers used in the composition in emulsion form are chosen from among those conventionally used in the area under consideration; The emulsifier and co-emulsifier are present in the composition in a proportion ranging from 0.3% to 30% by weight, preferably from 0.5% to 20% by weight with respect to the total weight of the composition. Among the oils which can be used according to the present invention, particular mention may be made of mineral oils, other vegetable oils (apricot oil, sunflower oil, plum oil), oils of animal origin, synthetic oils, siliconed oils and fluorinated oils (perfluoropolyethers). Fatty alcohols such as ketyl alcohol, fatty acids or waxes such as beeswax can also be used as fat according to the present invention. Among the emulsifiers and co-emulsifiers which may be used according to the present invention, particular mention may be made of fatty acid esters and esters of polyethylene glycol such as PEG-40 stearate or PEG-100 stearate, fatty acid and polyol esters such as glyceryl stearate and sorbitane tristearate. Among the hydrophilic gelling agents which can be used in the present invention particular mention may be made of carboxyvinyl polymers (carbomer) acrylic copolymers such as acrylate/alkylacrylate copolymers, polyacrylamides, polysaccharides, natural gums and clays. Among the lipophilic gelling agents particular mention may be made of modified clays such as bentones, metal salts of fatty acids, hydrophobic silica and polyethylenes.

The administering methods, dosages and optimal galenic forms of the compounds and compositions of the invention may be determined in accordance with criteria generally used when determining a pharmaceutical, veterinary, cosmetic or nutraceutical treatment, adapted to a patient or animal, such as age or body weight of the patient or animal, the seriousness of their general condition, tolerance to treatment, side effects encountered, skin type.

According to one variant of the present invention, the alkylfurans of the present invention may be incorporated, without any restriction, in food, drink and nutraceuticals, including dairy products (cheese, butter, milk and milk drinks, spreads containing milk products, ice creams and yoghurt), fat-based products (margarine, spreads, mayonnaise, cooking fat, frying oils and vinaigrettes), cereal-based products containing grains such as bread, pasta whether these foods are prepared, oven baked or processed, confectionery (chocolate, sweets, chewing gum, desserts, toppings, sorbets, glazings and other toppings), beverages whether alcoholic or not (sodas and other non-alcoholic drinks, fruit juices, food supplements, meal substitutes in drink form such as those sold under the trade names Boost™ and Ensure™) and various products (eggs, processed foods such as soups, ready-made sauces for pasta, ready-cooked dishes and other products of the same type). The composition of the present invention may be incorporated directly and without any other modification into food, nutraceuticals or drinks using techniques such as blending, infusion, injection, mixing, absorption, kneading and spraying. It is also possible for the consumer to apply the composition directly to food or drink before their consumption. These administering modes are easy and economical.

The following examples are non-limiting and are given by way of indication to illustrate the present invention.

EXAMPLE 1

Diabetic anti-blemish face cosmetic (Qty: 100 g)

|  | % |
|---|---|
| Water | 64.83 |
| Lupin peptide | 7 |
| Furanic unsaponifiable of avocado | 2 |
| Butylene glycol | 3 |
| Ketyl alcohol | 6 |
| Alkyl lactate C12-13 | 2 |
| Mineral oil | 7 |
| Ceteareth 20 | 2 |
| Stearic acid | 1 |
| Extract of white mulberry | 1 |
| Tocopherol acetate | 0.50 |
| Propylene glycol | 0.56 |
| Didosium EDTA | 0.52 |
| Triethanolamine | 0.80 |
| Preserving agent | 0.30 |
| Citric acid | 0.25 |
| Methyl paraben | 0.11 |
| Steareth-20 | 1 |
| Sodium metabisulfite | 0.05 |
| Sodium sulfite | 0.05 |
| Propyl paraben | 0.03 |

EXAMPLE 2

Cream for the skin comfort of diabetics (Qty: 100 g)

|  | % |
|---|---|
| Medicinal Vaseline | 6.00 |
| Hydrogenated palm oil | 4.00 |
| Glycerol caprylo caprate | 2.00 |
| Sucro ester 7 (sucrose distearate) | 6.00 |
| Squalane | 1.00 |
| Candelilla wax | 2.00 |
| Sucro ester 11 (sucrose stearate) | 0.50 |
| 2-alkylfuran | 2.00 |
| Sunflower concentrate | 2.00 |
| Glycerol | 5.00 |
| Glucodextrin | 1.00 |
| Tromethamine | 0.01 |
| Xanthan gum | 0.20 |
| Hydroxymethylglycinate A | 0.60 |
| Citric acid | 0.32 |
| Cyclomethiconol | 5.00 |
| Ceramide/Cholesterol | 0.60 |
| Purified water | 5.00 |

EXAMPLE 3

Protective cream for diabetic skin (Qty: 100 g)

|  | % |
|---|---|
| Squalane | 1.00 |
| Erythrityl ester | 4.00 |
| Decyl pentanoate | 4.00 |
| Cetearyl glucoside | 2.00 |

Protective cream for diabetic skin (Qty: 100 g)

|  | % |
|---|---|
| Lauryl ether 23 OE | 1.00 |
| Cutina CBSV | 1.00 |
| Beeswax | 0.50 |
| Myrista myristyl | 1.00 |
| Preserving agent | 0.30 |
| Thick vaseline | 5.00 |
| Gelled squalane | 3.00 |
| Furanic oil of avocado | 10.00 |
| Purified water | 56.51 |
| Phenoxyethanol | 0.80 |
| Sodium EDTA | 0.10 |
| Citric acid | 0.14 |
| Potassium sorbate | 0.45 |
| Glycerine | 5.00 |
| Thickener | 0.50 |
| Sodium hydroxide | 0.30 |
| Polyacrylamide gel 60° | 1.00 |
| Vitamin E acetate 35° | 0.50 |
| Perfume | 0.50 |
| Lupin peptide | 1.00 |
| Cyclomethyconol | 7.00 |
| Silica T1O2 | 1.00 |
| Genistein 85% | 0.10 |
| PEG 300 | 0.90 |

EXAMPLE 4

Foot cream (Qty: 100 g)

|  | % |
|---|---|
| Montanov | 68.3 |
| Amphisol K | 0.50 |
| Miglyol 812 | 6 |
| Preserving agent | 0.30 |
| Shea butter | 1 |
| Furanic oil of avocado | 1 |
| 2-alkylfuran | 5 |
| $Na_2$ EDTA | 0.10 |
| Citric acid | 0.01 |
| Preserving agent | 0.40 |
| Butylene glycol | 1 |
| Gelling agent | 0.25 |
| Sodium hydroxide | 0.4 |
| Manganese gluconate | 0.05 |
| Zinc salt | 0.10 |
| Purified water | to complete to volume |

EXAMPLE 5

Formulas for regulating glycaemia and hyper-cholesterolaemia

Hypercholesterolaemia and hypertriglyceridaemia

| Fenofibrate | 200 mg |
|---|---|
| Furanic unsaponifiable of avocado | 100 mg |
| Excipient for banded capsule | to complete to vol. |

Nutraceutical soft capsule to regulate weight gain and glycaemia

| Polyunsaturated fish fatty acids | 1000 mg |
|---|---|
| Furanic oil of avocado | 500 |
| Chromium | 1 |
| Pineapple | 50 |

-continued

| Formulas for regulating glycaemia and hyper-cholesterolaemia | |
|---|---|
| Apple pectin | 50 |
| Excipient | to complete to vol. |
| Hypolipaemic and anti-diabetic drug | |
| Atorvastatin | 10 to 40 mg |
| 2-alkylfuran | 33 to 100 mg |
| Excipient | to complete to vol. |
| Treatment of obesity | |
| Mucilage (sodium alginate) | 500 mg |
| Fish oil | 500 mg |
| Furanic unsaponifiable of avocado | 100 mg |
| Zinc salt | 1 mg |
| Orthosiphon | 325 mg |
| Fucus | 50 mg |
| Excipient for soft capsule | to complete to vol. |

EXAMPLE 6

| Nutraceutical powder (Qty: 100 g) | |
|---|---|
| Furanic unsaponifiable of avocado absorbed on cyclydextrin | 50.00 |
| Starch 1500 | 49.40 |
| Magnesium stearate | 0.60 |

EXAMPLE 7

| Slimming cream gel (Qty: 100 g) | |
|---|---|
| | % |
| Carbopol Etd 2020 | 0.6 |
| Xanthan gum | 0.15 |
| Genistein 85% | 0.1 |
| Alcohol + Caffeine | 3.6 |
| NaOH | 0.001 |
| Preserving agent | 0.9 |
| Unsaponifiable of avocado | 2 |
| Glucodextrin | 2 |
| Perfume | 0.7 |
| Silicon | 0.3 |
| Purified water | to complete to vol. |

EXAMPLE 8

| Hygienic wipes for diabetic feet (Qty: 100 g) | |
|---|---|
| | % |
| Poloxamer 184 | 1.0000 |
| Perfume | 0.2000 |
| Purified water | 91.1550 |
| PEG-32 | 4.0000 |
| Preserving agent | 1.0000 |
| Chlorhexidin | 0.1500 |
| Phenoxyethanol | 0.1000 |
| Allantoin | 0.2000 |
| 2-Alkylfuran | 1.0000 |

-continued

| Hygienic wipes for diabetic feet (Qty: 100 g) | |
|---|---|
| | % |
| Solubiliser | 1.0000 |
| Tromethamine | 0.1950 |

EXAMPLE 9

Study on the Effects of 2-Alkylfurans on the Metabolism

1) Tested Product

The purified furanic fraction of unsaponifiable avocado tested is marketed by Laboratoires Expanscience under the trade name Avocadofurane® (AV102) containing 98 weight % of 8-11-cis-cis-heptadecadienyl-2-furan.

2) Experimental Protocol

We used adult mice (aged 6 weeks) of masculine gender fattened on a high fat/high sucrose diet (HF/HS). Feeding with the HF/HS diet began on mice aged 6 weeks and continued throughout the period of the study. The study was conducted along 2 axes:

prevention: the product was administered as soon as feeding began with the HF/HS diet;

management (curative): the product was administered 12 weeks after the start of the HF/HS diet.

Total treatment time (preventive and curative): 23 weeks.

Each experimental group comprised 10 mice. For this study 8 experimental groups were set up:

2 control groups:
negative control: the mice were given a normal diet
positive control: the mice were given a HF/HS diet 2 reference groups
HF/HS+TZD diet (thiazolidine-dione (Rosiglitazone-PPARα agonist): 10 mg/kg/day
HF/HS diet then after 12 weeks TZD at 10 mg/kg/day 2 treatment groups:
HF/HS diet+0.1 wt. % AV 102 with respect to total weight of the diet
HF/HS diet+AV102 at a weight concentration of 0.25%

Each study started at D-7 (i.e. 7 days before the start of the HF/HS diet) with an analysis of glucose tolerance using either an intra-peritoneal glucose tolerance test for some of the animals (n=5) or a sensitivity test to intravenous insulin for the other animals (n=5). At D=0 blood samples were taken to obtain basal condition values for all lipid and lipoprotein parameters, then the mice were randomly distributed irrespective of weight. The weight of each mouse and the quantity of food absorbed were measured twice a week. At weeks 3, 8, 15 and 23 the blood was collected after overnight fasting. At weeks 12 and 18 some of the animals (n=5) were subjected to an intra-peritoneal glucose tolerance test, the others (n=5) to a sensitivity test to intravenous insulin. At week 19 faecal matter was collected for analysis of lipid composition (triglyceride measurement). At week 14 (preventive) and week 20 (preventive and curative) a Dexascan analysis was performed on the anaesthetised animals to measure bone mineral density, skeleton weight and fat content. At weeks 21 and 22 energy expenditure was measured by indirect calorimetry. At the end of the study (week 23) the animals were sacrificed and their livers, intestines, adipose tissue and muscles were recovered, weighed, frozen and stored at a temperature of −80° C. for additional analyses. The liver and adipose tissue were also prepared for histological analysis.

At weeks 3, 8, 15 and 23 the following blood tests were performed: plasma lipids (total cholesterol, triglycerides, High Density Lipoprotein (HDL) "good" cholesterol, Low Density Lipoprotein (LDL) "bad" cholesterol, free fatty acids); glucose and insulin; leptin, TNF-α; transaminases and alkaline phosphatase (liver toxicity). Subsequently the following were analysed: lipoprotein profile (by size exclusion chromatography); apolipoportein A1; lipid composition of the liver (liver triglycerides, cholesterol and free fatty acids); histological analysis of the liver and adipose tissue; staining of accumulated lipids in the liver.

3) Results

The doses of AV102 theoretically absorbed by the mice are 160 mg/kg/day of 0.1% AV102 (25 g mouse eating 4 g of food/day) and 400 mg/kg/day (25 g mouse eating 4 g of food/day). The doses effectively ingested by the mice during the curative phase and prevention phase are given in Table 2 below:

TABLE 2

Doses of AV102 ingested by mice (curative and preventive)

| | Curative phase | Prevention phase |
|---|---|---|
| AV102 (0.1%) | 94 ± 10 mg/kg/day | 136 ± 24 mg/kg/day |
| AV102 (0.25%) | 183 ± 42 mg/kg/day | 314 ± 72 mg/kg/day |

1. Food Intake and Weight Gain

It was verified that the different treatments did not have an influence on normal feeding of the mice. It was also found that the mice on the HF/HS diet with AV102 (0.1% or 0.25%) lost weight. The results are given in Table 3 below:

TABLE 3

Food intake - weight of mice on HF/HS diet

| | Preventive | | Curative | |
|---|---|---|---|---|
| | Food | Mouse wt. | Food | Mouse wt. |
| TZD (10 mg/kg/dy) | ↓ | — | ↓ | — |
| AV102 (0.1%) | — | ↓ (14 weeks) | — | ↓ (14 weeks) |
| AV102 (0.25%) | ↓ | ↓↓↓ (1 week) | ↓ | ↓↓↓ (3 days) |

In Table 4 below, the ratio is given of the weight of the mice on different HF/HS diets (normal diet/HF/HS diet only/HF/HS diet with TZD and HF/HS diet with 0.1% or 0.25% AV102) after 20 weeks' treatment, to the weight of these mice before treatment (preventive Week 0, curative Week 12).

TABLE 4 weight of mice on HF/HS diet

| | Negative control | Positive control | TZD 10 mg/kg/day | AV102 0.1% | AV102 0.25% |
|---|---|---|---|---|---|
| Preventive: Ratio Week 20/Week 0 | 1.33 | 1.54 | 1.66 | 1.37 | 1.05 |
| Curative: Ratio Week 20/Week 12 | 1.03 | 1.12 | 1.17 | 1.02 | 0.76 |

Food Intake

Preventive group: near-normal consumption was observed in mice on the HF/HS diet with 0.1% AV102 (±3.7 grams). Normal consumption was observed up to D56, then a slight reduction followed by a return to normal at the end of treatment in mice on the HF/HS diet with 0.25% AV102 without any impact on results (mean consumption 3G:ditto TZD).

Curative group: an impact of the active ingredients was observed, and especially of 0.25% AV102 (4 g control group, 3 g TZD 0.1% AV102, 2.5 g 0.25% AV102).

Weight Gain

Preventive group: in the mice on the HF/HS diet with 0.1% AV 102, a 11% reduction in weight was observed in said mice; i.e. a return to normal weight. In mice on the HF/HS diet with 0.25% AV102, a weight reduction of 32% was observed in said mice; at the end of treatment, the weight of these mice was lower than the weight of the mice on a normal diet.

→AV102 opposes weight gain and causes substantial weight loss on a HF/HS diet, as early as the first days of treatment at a concentration of 0.25%.

Curative group: On a HF/HS diet only, the mice gained 12% weight. The addition of TZD to their food did not cause the overweight mice to lose weight. The addition of 0.1% AV102 to their food brought a 11% weight reduction with a return to normal weight. The addition of 0.25% AV102 gave rise to a 33% weight reduction in the mice, i.e. a substantial weight loss compared to normal.

→AV102 causes initially overweight mice to lose weight under a dose/time effect (almost immediate) which can lead to a substantial weight loss.

2. Blood Parameters

Lipids

The different cholesterol blood levels and different fractions were analysed using a HPLC method.

TABLE 5

| | | TZD (10 mg/kg/day) | | 0.1% AV102 | | 0.25% AV102 | |
|---|---|---|---|---|---|---|---|
| PREVENTIVE | Total cholesterol | ↓↓ (3W***) | | Total cholesterol | ↑ | Total cholesterol | ↑ |
| | LDL | — | | LDL | ↑↑ (3W***) | LDL | ↑↑ (3W***) |
| | HDL | ↓↓ (3W***) | | HDL | — | HDL | — |
| | TG | ↓ | | TG | ↓ | TG | ↓↓↓↓ (3W***) |
| | FFA | — | | FFA | — | FFA | — |

TABLE 5-continued

| CURATIVE | TZD (10 mg/kg/day) | | 0.1% AV102 | | 0.25% AV102 | |
|---|---|---|---|---|---|---|
| | Total cholesterol | ↓↓ (3W***) | Total cholesterol | ↑ | Total cholesterol | ↑ |
| | LDL | ↓ | LDL | ↑↑ (3W**) | LDL | ↑↑ (11W**) |
| | HDL | ↓↓ (3W***) | HDL | ↑↑ (3W***) | HDL | — |
| | TG | — | TG | — | TG | ↓↓↓↓ (11W***) |
| | FFA | — | FFA | ↓↓ (11W***) | FFA | ↓↓ (11W***) |

W = Week
TG = Triglycerides
FFA = Free fatty acids

Preventive group: a significant reduction in total cholesterol, HDL cholesterol levels was observed after 3, 8, and 23 weeks of treatment with TZD. The LDL cholesterol levels also showed a downward trend in this group. This decrease is also found in plasma lipoprotein profiles which show a reduction in HDL, LDL and VLDL (Very Low Density Lipoprotein) cholesterol fractions at weeks 8 and 15.

Total cholesterol increased in mice treated with 0.1% AV102 after 3 and 15 weeks of treatment, and in mice treated with 0.25% AV120 after 3, 15 and 23 weeks of treatment. The lipoprotein profiles, weeks 8 and 15, showed an increase in the HDL cholesterol fraction and a reduction in the LDL and VLDL cholesterol fractions in mice treated with AV102 at both doses.

The plasma levels of triglycerides were significantly reduced after 8 weeks of treatment with TZD and 0.1% AV102, but no additional reduction was observed after 15 and 23 weeks of treatment with these products. A significant reduction in cholesterol levels was observed after 3, 8, 15 and 23 weeks of treatment with 0.25% AV102.

The levels of free fatty acids did not show any significant variation.

Curative group: a reduction in total cholesterol, in HDL and LDL cholesterol levels was observed after 3 and 11 weeks of treatment with TZD. The lipoprotein profiles of these mice also showed a reduction in the fractions of HDL and VLDL cholesterol after 3 weeks' treatment.

Total cholesterol tended towards an increase in mice treated for 3 and 11 weeks with AV102 at both doses. The lipoprotein profiles of the mice treated with 0.25% AV102 for 11 weeks showed an increase in the LDL cholesterol fraction and a reduction in the HDL and VLDL cholesterol fractions.

The triglyceride levels were significantly reduced in mice treated with 0.25% AV102 after 3 and 11 weeks. No change in the triglyceride level was observed with TZD and 0.1% AV102.

The levels of free fatty acids were reduced after 10 weeks of treatment with AV102 at both doses.

Therefore Avocadofurane, especially at 0.25%:
prevents the rise and causes a very significant reduction in triglycerides both preventively and curatively,
increases total cholesterol, HDL, and reduces LDL, VLDL
TZD has little or no action on TGs but it reduces total cholesterol.
Glucose
A-Blood glucose analysis Preventive group: The glucose levels were reduced in each group treated after 3 weeks. At weeks 8, 15 and 23 this reduction was still observed in mice treated with AV102, at both treatment doses; on the other hand this reduction was no longer observed in the mice treated with TZD.

TZD reduces "constitutive" hyperglycaemia with a return to normal. AV102, at a dose of 0.25%, acts very significantly and more efficiently than TZD.

If consideration is given to the percentage development of glycaemia in the different groups compared with the glycaemia of the normal diet group at 3 and 23 weeks, all the active ingredients have an action on the hyperglycaemia caused by the rich diet. AV102 is the compound whose dose-effect activity is extended throughout the length of the study in highly significant manner.

Curative group: the glucose levels dropped considerably after 3 and 11 weeks of treatment with TZD and 0.25% AV102.
B-Glucose resistance (IPGTT)
IPGTT=Intraperitoneal Glucose Tolerance Test (fasting).
Very high disturbed tolerance to glucose is seen to prevail in obese children. In addition this prevailing tolerance is often accompanied by insulin resistance.

Protocol:
fasted mice,
measurement of glycaemia at TO,
intra-peritoneal injection of glucose,
measurement of glycaemia 15, 30, 45, 60, 90, 120 and 180 min. after injection,
kinetics performed weeks 1, 12 and 18 in the preventive group and week 18 in the curative group.

Preventive group: the results of the IPGTT test show a reduced Area Under Curve value (AUC) in mice on the HF/HS diet+0.25% AV102 at weeks 12 and 18. There is no significant AUC reduction in mice on the HF/HS diet with TZD.

The HF/HS diet increases glucose resistance. TZD reduces glucose resistance: AUC value intermediate between HF/HS and normal diet at 12 weeks. At 18 weeks, TZD completely cancels out the effects of the HF/HS diet with a return to normal kinetics. 0.1% and 0.25% AV102: significant reduction, greater than with TZD, in glucose resistance versus HF/HS at 12 and 18 weeks. On this date the curve lies below normal kinetics.

Curative group: the results of the IPGTT test have the same profile as the results observed in the preventive group: a reduced AUC is seen in mice treated with 0.25% AV102 for 6 weeks.

The HF/HS diet induces a strong resistance to glucose. TZD does not act on already established, diet-induced glucose resistance. 0.1% and 0.25% AV102 act most significantly, with a dose effect, on this resistance.

C—Insulin Sensitivity (Preventive Group)

Diabetics suffer from an increase in insulin resistance which leads to hyperglycaemia. The test used is the Intra Peritoneal Insulin Sensitive Test—IPIST.

Protocol:
fasted mice,
measurement of glycaemia at T0,
intra-peritoneal injection of insulin,
measurement of glycaemia 0, 15, 30, 45, 60 and 90 min. after the injection,
kinetics performed weeks 1 and 12 in the preventive group The HF/HS diet reduces sensitivity to insulin. TZD restores sensitivity to insulin (15 min). A significant increase in insulin sensitivity is observed in mice treated with 0.1% and 0.25% AV102.

The different results are summarized in Table 6 below:

TABLE 6

Impact of glucose on the metabolism

|  | TZD (10 mg/kg/day) |  | 0.1% AV102 |  | 0.25% AV102 |  |
| --- | --- | --- | --- | --- | --- | --- |
| PREVENTIVE | GLUCOSE | ↓ | GLUCOSE | ↓↓ (3W***) | GLUCOSE | ↓↓ (3W***) |
|  | IPGTT | — | IPGTT | — | IPGTT | ↓↓ (12W***) |
|  | IPIST | ↓↓ (3W***) | IPIST | — | IPIST | — |
|  | INSULIN | ↓ | INSULIN | ↓ | INSULIN | ↓ |
| CURATIVE | GLUCOSE | ↓↓ (3W**) | GLUCOSE | — | GLUCOSE | ↓↓ (3W***) |
|  | IPGTT | — | IPGTT | — | IPGTT | ↓↓ (6W**) |
|  | IPIST | — | IPIST | — | IPIST | — |
|  | INSULIN | — | INSULIN | — | INSULIN | — |

W = week

To conclude, (impact of glucose on the metabolism), avocadifurane can be used:
to reduce glycaemia in pre-diabetic mice,
to remedy impaired glucose tolerance induced by a HF/HS diet, and
to restore insulin sensitivity.

Avocadofurane allows better regulation of the glucose metabolism than TZD in pre-diabetic and obese mice.

Hepatic Metabolism

The transaminases (ALAT and ASAT) are not modified by the different treatments. An increase in alkaline phosphatase (ALP) was seen in all groups. It is particularly high in the 0.25% AV102 group. It is to be noted that in the control groups ALP showed a most significant decrease throughout the study, this no doubt being a reflection of the reduced bone turnover related to ageing of the animals.

The increase in plasma ALP in the TZD and AV102 groups, which incidentally can be considered very moderate, does not appear to reflect liver toxicity since the other liver enzymes (ALAT and ASAT) were not modified by the different treatments. This result would appear to correlate more with the reduced bone density evidenced by Dexascan.

3. Fats

Preventive group: The body fat index of the animals was significantly reduced with AV102 at 314±72 mg/kg/day (14 and 20 weeks) and 136±24 mg/kg/day (20 weeks). TZD had no effect on this parameter. A reduction in leptin was also observed with both doses of AV102.

Curative group: the body fat index dropped after 8 weeks of treatment with AV102 at 183±42 mg/kg/day, but not at 94±10 mg/kg/day. No effect on leptin was observed.

4. Other Parameters
Bone density: reduced in the preventive group (for both doses) at 14 and 20 weeks, and in the curative group (0.25% AV102);
Body temperature: no change in the preventive group. Slight increase in the curative group with TZD and AV102.
Energy expenditure (calorimetry): no change.
Triglycerides: significant reduction with AV102 in the liver and muscles (preventive: 0.25% AV102, and curative: 0.25% AV102). In the preventive group, increase in the faeces with 0.1% AV102.

5. Weight of Tissues

Preventive group: a significant reduction (>TZD) was observed in the weight of brown adipose tissue with AV102 (dose-dependent effect). No change was observed in liver weight in absolute terms. Again in absolute terms, a reduction in muscle mass was observed with TZD and AV102 (AV102>TZD).

Curative group: in mice treated with 0.25% AV102 a significant reduction was observed in the weight of brown adipose tissue. In absolute terms, no change was observed in liver weight. If the absolute values of muscle mass are compared, there is no significant difference between the different groups.

6. Histology

In the preventive and curative groups, a reduction in the accumulation of lipids was observed in the liver of mice treated with 0.25% AV102.

Labelling of mitochondria: increased labelling was observed in all groups treated versus HF/HS. The strongest effect was seen with 0.25% AV102 in the curative group.

7. Analysis of mRNAs

In the liver, the mRNA expressions of 8 genes were determined in 5 mice of each group using real-time Q-RT-PCR analysis. The results are given in Table 7.

TABLE 7 analysis of mRNAs in the liver

| LIVER | TZD | AV102 (0.25%) |
|---|---|---|
| ACO (target PPARα) | ↑ | ↑↑↑ |
| PEPCK (target PPARγ) | ↑ | ↑↑↑ |
| GSH-S-transferase (target PXR) | ↑ | ↑ |
| CYP7A1 (conversion oxysterol into biliary acids) | ↑↑ | ↑↑ |
| ME, FAS, ACC (fatty acid synthesis) | ↑↑ | ↑↑ |

ACO = acetyl coA oxidase
PEPCK = phosphoenolpyruvate carboxykinase
GSH-S-transferase = Glutathion-S-transferase
CYP7A1 = Cytochrome P450 7A1
ME = malic enzyme,
FAS = Fatty acid synthesis
ACC = Acetyl-CoA carboxylase 0.25% AV102 activates the PPARα and PPARγ agonists in vivo. 0.25% AV102, like TZD, also activates PXR. Finally, 0.25% AV102 increases the expression of the enzymes involved in the metabolism of lipids and glucose to normalize the pathological effects induced by the HF/HS diet.

In the brown adipose tissue (BAT) and in the muscles, the mRNA expression of 3 genes was determined in 5 mice of each group by real-time Q-RTR-PCR analysis. The results are given in Table 8.

TABLE 8

Analysis of mRNAs in the muscles and BAT

| MUSCLE/BAT | TZD | AV102 (0.25%) |
|---|---|---|
| UCP-1 (thermogenesis) | — | — |
| PGC-1 (mitochondria biogenesis) | ↑ (muscle) | ↑ (muscle) |
| GSH-S-transferase (target PXR) | ↑ | ↑ |
| MCPT-1 (target PPARα) entry of fatty acids into the mitochondria) | — | ↑↑ (adipose tissue) |

UCP-1 = Uncoupling protein-1
PGC-1 = co-activator-1 PPARγ
MCPT-1 = Muscle-type carnitine palmitoyltranferase-1

0.25% AV102 promotes beta-oxidation in BAT. In addition, an increase in the expression of PGC-1 in the muscles can contribute towards an increase in mitochondria in the muscles.

4) Conclusion

AV102: prevents weight gain on a HF/HS diet, reduces the weight of obese mice on a HF/HS diet, reduces TGs in the liver and muscles, reduces blood glucose and increases glucose tolerance, has effects on cholesterol which are contradictory but increases good cholesterol and reduces bad cholesterol, induces the expression of target PPARα and γ genes in the liver and brown adipose tissue. In the muscle has a tendency to increase PGC-1 which could account for the increased labelling of mitochondria in the muscle. In addition, AV102 is well tolerated.

To conclude, a diet high in furan can limit the risk of overweight or obesity in Type II diabetes and dyslipidaemia; this should translate as a concomitant drop in cardiovascular risk.

In man, the doses which can be considered are approximately 60 mg/day of AV102, i.e. approximately 0.86 mg/kg/day of AV102 or approximately $2.8 \cdot 10^{-6}$ mole/kg/day of AV102.

The invention claimed is:

1. A method for treating obesity and overweight comprising the administration of an effective amount of one or more, synthetic or natural alkylfurans, of general formula (I):

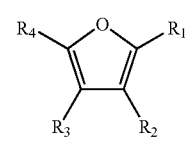

wherein $R_1$, $R_2$, $R_3$ and $R_4$ represent independently of each other a radical selected from the group consisting of a hydrogen, a $C_1$-$C_{35}$ alkyl, a $C_1$-$C_{35}$ alkenyl, or a $C_1$-$C_{35}$ alkynyl, to an obese or overweight patient.

2. The method according to claim 1, wherein $R_1$, $R_2$, $R_3$ and $R_4$ represents independently of each other a radical selected from the group consisting of a hydrogen, a $C_{10}$-$C_{22}$ alkyl, a $C_{10}$-$C_{22}$ alkenyl, and a $C_{10}$-$C_{22}$ alkynyl.

3. The method according to claim 1, wherein said alkyls, alkenyls and alkynyls are substituted with one or more halogens and/or with one or more functions selected from the group consisting of epoxide, hydroxyl (—OH), thiol (—SH), ether (—OR$_5$), primary amine (—NH$_2$), secondary amine (—NHR$_5$), tertiary amine (—NR$_5$R$_6$), acetyl (—O—CO—R$_5$) functions, with $R_5$ and $R_6$ representing independently of each other a radical selected from the group consisting of a hydrogen, a $C_1$-$C_{35}$ alkyl, or a $C_1$-$C_{35}$ alkenyl.

4. The method according to claim 3, wherein $R_5$ and $R_6$ represents independently of each other a radical selected from the group consisting of a hydrogen, a $C_{10}$-$C_{22}$ alkyl and a $C_{10}$-$C_{22}$ alkenyl.

5. The method according to claim 1, wherein said alkylfurans are 2-alkylfurans described by the general formula (I) wherein $R_1$, $R_2$, $R_3$ represent a hydrogen and $R_4$ represents a radical selected from the group consisting of $C_1$-$C_{35}$ alkyl, a $C_1$-$C_{35}$ alkenyl, or a $C_1$-$C_{35}$ alkynyl.

6. The method according to claim 5, wherein $R_4$ represents a radical selected from the group consisting of a $C_{10}$-$C_{22}$ alkyl, a $C_{10}$-$C_{22}$ alkenyl, or a $C_{10}$-$C_{22}$ alkynyl.

7. The method according to claim 5, wherein said alkyls, alkenyls and alkynyls are substituted with one or more halogens and/or with one or more functions selected from the group consisting of epoxide, hydroxyl (—OH), thiol (—SH), ether (—OR$_5$), primary amine (—NH$_2$), secondary amine (—NHR$_5$), tertiary amine (—NR$_5$R$_6$), acetyl (—O—CO—R$_5$) functions, with $R_5$ and $R_6$ representing independently of each other a radical selected from the group consisting of a hydrogen, a $C_1$-$C_{35}$ alkyl, or a $C_1$-$C_{35}$ alkenyl.

8. The method according to claim 7, wherein $R_5$ and $R_6$ represents independently of each other a radical selected from the group consisting of a hydrogen, a $C_{10}$-$C_{22}$ alkyl and a $C_{10}$-$C_{22}$ alkenyl.

9. The method according to claim 1, wherein said alkylfurans are natural 2-alkylfurans, described by general formula (I) wherein $R_1$, $R_2$, $R_3$ represent a hydrogen and $R_4$ represents a radical selected from the group consisting of the following radicals (*—$R_4$):

-continued
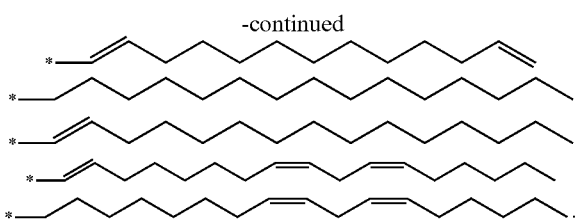
10. The method according to claim 9, wherein said alkylfurans are natural 2-alkylfurans present in furanic unsaponifiable of avocado.
11. The method according to claim 9, wherein said natural 2-alkylfurans derive from a purified furanic fraction from unsaponifiable of avocado.
* * * * *